United States Patent [19]

Schoolman

[11] Patent Number: 4,936,318

[45] Date of Patent: Jun. 26, 1990

[54] VACUUM BARRIER

[75] Inventor: Arnold Schoolman, Kansas City, Mo.

[73] Assignee: Schoolman Scientific Corporation, Kansas City, Mo.

[21] Appl. No.: 352,461

[22] Filed: May 16, 1989

[51] Int. Cl.[5] .......... A61L 9/16

[52] U.S. Cl. .......... 128/847; 128/917; 128/918; 128/849; 15/301; 98/115.4

[58] Field of Search .......... 219/137.41; 15/300 R, 15/301; 98/115.1, 115.3, 115.4; 128/846, 849, 863, 847, 917, 918

[56] References Cited

U.S. PATENT DOCUMENTS

| | | | |
|---|---|---|---|
| 3,516,232 | 6/1970 | Gilbertson | 98/115.1 |
| 3,537,447 | 11/1970 | Gauthier et al. | 128/847 |
| 3,880,061 | 4/1975 | Hensiek | 98/115.1 |
| 3,881,477 | 5/1975 | Von Otto | 128/847 |
| 4,045,192 | 8/1977 | Eckstein et al. | 98/115.1 X |
| 4,055,173 | 10/1977 | Knab | 128/847 |
| 4,062,274 | 12/1977 | Knab | 98/115.4 |
| 4,082,092 | 4/1978 | Foster | 128/847 |
| 4,109,144 | 8/1978 | Vidmar | 98/115.4 X |
| 4,140,105 | 2/1979 | Deuvlis | 128/847 |
| 4,197,646 | 4/1980 | Morrison | 98/115.1 X |
| 4,223,669 | 9/1980 | Morledge | 128/847 |
| 4,252,054 | 2/1981 | Bakels | 433/92 |
| 4,446,861 | 5/1984 | Tada | 128/863 |
| 4,490,881 | 1/1985 | Schmidt | 15/301 |
| 4,594,747 | 6/1986 | Dempsey | 15/301 |
| 4,596,060 | 6/1986 | Schmidt et al. | 98/115.4 X |
| 4,607,413 | 8/1986 | Schmidt et al. | 98/115.4 X |
| 4,647,295 | 3/1987 | Christ | 15/301 X |
| 4,650,171 | 3/1987 | Howorth | 269/322 |

FOREIGN PATENT DOCUMENTS

| | | | |
|---|---|---|---|
| 1023242 | 3/1953 | France | 98/115.4 |
| 2334432 | 7/1977 | France | 98/115.4 |

OTHER PUBLICATIONS

Abstract, German Petty Patent, 7,736,347 Klasse B 08.

*Primary Examiner*—Robert A. Hafer
*Assistant Examiner*—Kevin G. Rooney
*Attorney, Agent, or Firm*—Litman, McMahon & Brown

[57] ABSTRACT

A protective apparatus for preventing the exchange of harmful substances between an area isolated by the apparatus and the environment for use in medical, laboratory, and industrial application. The apparatus includes a physical shield, a vacuum barrier, and an adjustable support frame. The apparatus further includes a vacuum connector for connecting the apparatus to a vacuum source, a vacuum conduit for flow communicating with the air around the perimeter of the physical shield such that the vacuum source draws air along with solid and liquid matter entrained in the air into the vacuum conduit, and a plurality of vacuum apertures located along the vacuum conduit for communicating the vacuum source with the air. The apparatus is designed so as to provide protection for persons in proximity to a source of harmful substances such as aerosols produced by surgical procedures at a surgical incision on a patient infected with the AIDS virus or the like.

16 Claims, 2 Drawing Sheets

VACUUM BARRIER

BACKGROUND OF THE INVENTION

The present invention relates to devices for reducing or preventing the discharge of harmful substances from an area isolated by such a device to the surrounding environment.

Foreseeable applications for the present invention especially include the isolation of air contaminated by potentially disease-carrying blood or airborne aerosol particles from a patient during a medical procedure, but can also include applications in laboratories, industrial environments and the like, where the isolation of an area for health and safety reasons is desirable and unobstructed manual access is necessary. In particular, such a device is needed where it is necessary for a surgeon or other person to have generally open manual access to the area, yet where protection is required to prevent fluids such as blood from spraying into the face of the person and to prevent other fluids in the form of aerosols or the like and containing infectious material from escaping into the room surrounding the area.

The present invention is especially useful in the medical area for preventing the escape of harmful substances from the site of medical procedures such as surgical incisions, and the like. Harmful substances of concern in the medical area include, but are not limited to, blood and other body fluids (which often form fine aerosols in the air during procedures requiring drilling or cutting), small particles of skin, fat or muscle tissue and bone particles which are contaminated. Such substances may be contaminated by hepatitis, acquired immune deficiency syndrome (AIDS), or other transmittable diseases. Medical procedures especially dangerous to operating room personnel are those using endoscopes and bone cutting devices such as drills, reamers, saws and similar devices which may cause harmful substances to become airborne. Such airborne substances may come in contact with an open cut, a mucous membrane, or the like of the medical practitioner such that the practitioner becomes infected or contaminated by the substances.

Currently, surgical garments and masks are used as the primary protection for operating room personnel. Surgical garments and masks are not intended to, and do not prevent, the spread of harmful substances and organisms to all parts of the general operating room environment and do not protect certain parts of the practitioner. For example, such equipment often does not protect the eyes and other exposed parts of the body of operating room personnel from contact with fluids in the form of airborne aerosols including bone particles and liquids or from direct sprays, streams, or splashes of liquids. Infections and contagious body fluids are of particular concern, especially in the region of the head.

A second category of protective devices in use in the medical area is protective hoods incorporating a vacuum system used to draw away anesthetic gases from the mouths of patients during oral surgery and dentistry. Typically, the hoods are mounted on the end of a free-standing boom or on an arm attached to a dentistry chair. In operation, the dentist or oral surgeon positions the hood over the mouth of the patient during or after administration of anesthesia and activates the vacuum generation means to evacuate the gases.

Such hoods are limited in use and there are numerous limitations in the ability of these hoods to be adapted to protect medical and dental personnel from airborne infectious material emanating from the patient in a general operating room environment.

First, the hoods are limited in size as they are intended to remove only the small amount of gases such as those present during oral surgery and dentistry. The small size of the hoods limits the adaptability thereof to provide a sufficient physical barrier to block streams and sprays of body fluids and to contain the airborne particles generated during large scale surgical procedures such as joint replacement. Enlarging the size of the physical barrier would generally require abandonment of the current support structure for one similar to that of the present invention. Additionally, the dental hoods have a centrally located vacuum system and do not provide vacuum around the periphery of the hood, providing only incomplete protection against the escape of harmful gases and the like. Again, enlarging of the size of the dental hoods for use in general surgery and the like would require substantial redesign of the evacuation system.

Second, the hoods are not completely or substantially transparent, generally containing only a small window, if transparent at all. If the hoods were enlarged for surgical use and the like, the visual obtrusiveness of the hoods would significantly impair the ability of surgeons and support staff to have unobstructed access to the incision, as maximum protection is afforded only when the hood is positioned in close proximity to the incision and extends over a wide area.

Finally, as mentioned earlier, the hoods provide only a single vacuum aperture. A single vacuum aperture would not have the capability to provide a vacuum barrier around the perimeter of an area contemplated to be isolated and, consequently, it would be difficult to contain gases with such a device.

A third type of protective device in use in the medical area is an autopsy table incorporating a series of variable position vacuum ducts along the sides of the table, or alternatively, air supply ducts on one side of the table and vacuum ducts on the opposing side. In operation, the ducts draw a flow of air across the table so as to vent away noxious gases. At the head of the autopsy table, two opposing ducts may be positioned at the same height and a transparent table placed thereon.

Limitations of the autopsy table with respect to adaptability for the purposes of the present invention include the lack of vacuum ducts around the entire perimeter of the site of the medical procedure. Such openings in the vacuum barrier provide routes of escape for gases and aerosolized liquids not captured in the cross-flow due to obstructions of flow such as those occurring when persons reach into the cross-flow. Secondly, access to the site is limited on two sides due to the vacuum ducts and supplies that effectively form an access barrier. Additionally, the angle of the table is not variable and the configuration is not portable or free-standing.

Certain other conventional protective devices provide only a physical barrier or only a vacuum barrier but not a combination of the two. Those providing only a physical barrier generally are either too obtrusive to the surgeon's work area or do not prevent the escape of gases and vapors into the general operating room environment. For example, surgical garments that resemble astronaut's space suits which protect only the person wearing it provide no protection for the environment or others. Protective devices generating only vacuum to draw airborne substances, as is obvious, provide no physical barrier to streams or sprays of fluids.

Finally, vacuum devices currently in use and having self-contained vacuum source are often limited in application, as such devices incorporate no means for the containment, destruction, or safe evacuation of contaminants. Such devices are inappropriate for protection from hepatitis and AIDS as those viruses are dangerous in low concentrations and could be carried to remoter sites by an evacuation system that does not remove contaminants from the gas stream. Devices which merely dilute the concentration of toxic substances are clearly inadequate for the task of removal of infectious materials from the air.

OBJECTS OF THE INVENTION

Therefore, the objects of the present invention are: to provide a protective apparatus that incorporates both physical and vacuum barriers; to provide such an apparatus that is of sufficient size to cover an entire site of a medical procedure, and provides for destruction or disposal of harmful substances; to provide such an apparatus that is portable and easily adjusted to fit the requirements of each different usage; to provide such an apparatus providing a clear shield surrounded by apertures connected to a vacuum generating system and drawing fluids therethrough; to provide such an apparatus which is relatively simple to use, inexpensive to produce and which is especially well adapted for the intended usage thereof; and to provide a method for isolating the immediate area around a medical, laboratory, or industrial procedure site utilizing such an apparatus.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE INVENTION

Figure 1:
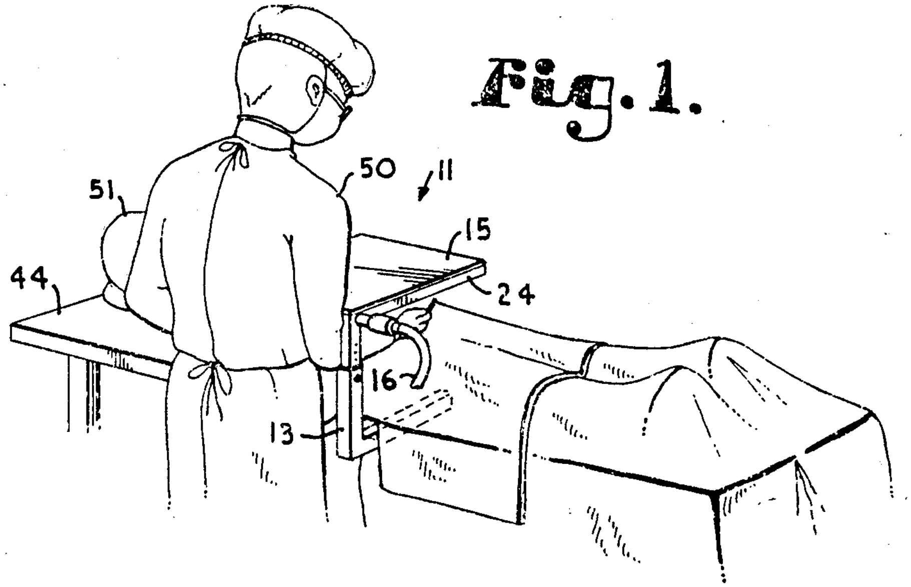
FIG. 1 is a perspective view of a protective apparatus in accordance with the present invention shown in conjunction with an operating table having a patient thereon and a surgeon performing a medical procedure.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

A protective apparatus in accordance with the present invention is generally designated by the reference numeral 11. The protective apparatus 11 generally comprises a support structure 13, a hinged transparent shield 15, pivotally mounted on the support structure 13, and a vacuum drawing system 16. The vacuum drawing system 16 includes a vacuum conduit 17, a vacuum channel member 18 positional about the shield 15, and a vacuum generator 19 flow connected to the channel member 18 by the vacuum conduit 17.

Figure 3:
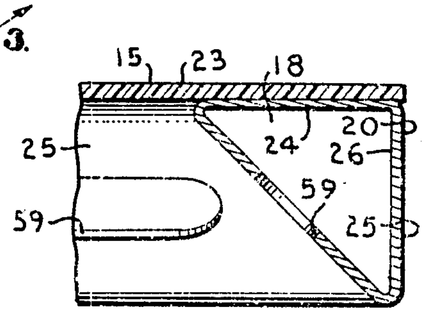
FIG. 3 is an enlarged and fragmentary cross-sectional view of the apparatus, taken along line 3—3 of FIG. 2 and showing a vacuum conduit thereof.

The support structure 13 includes a frame 20 and a pair of legs 21 and 22 pivotally connected thereto. The frame 20 is generally rectangular and rigid with a central panel 23 and a triangular cross-sectional tubular member 24, surrounding and under the periphery of the panel 23, see FIG. 3. The cross-section of the tubular member 24 approximately defines a right triangle with a hypotenuse thereof oriented at approximately a 45 degree angle to a plane associated with the panel 23.

The tubular member 24 includes four sections 25 connected at approximately a 90 degree angle to one another with joints providing airtight and unobstructed communication between inner cavities of the adjacent sections 25. The unobstructed connections between the sections, combined with the tubular construction of member 24 define an inner continuous passage or channel 26 operably functioning as the vacuum channel member 18.

Figure 2:
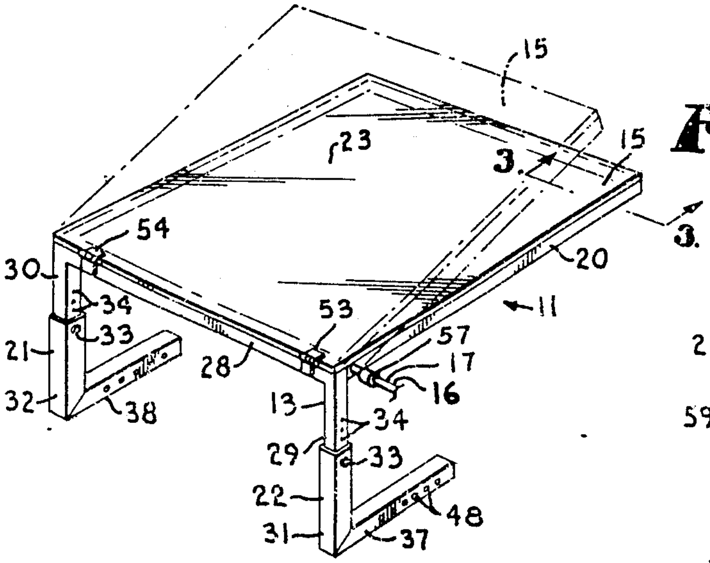
FIG. 2 is an enlarged perspective view of the apparatus showing a transparent shield thereof in a generally horizontal orientation and also showing the shield in an alternate orientation in phantom lines.
Figure 4:
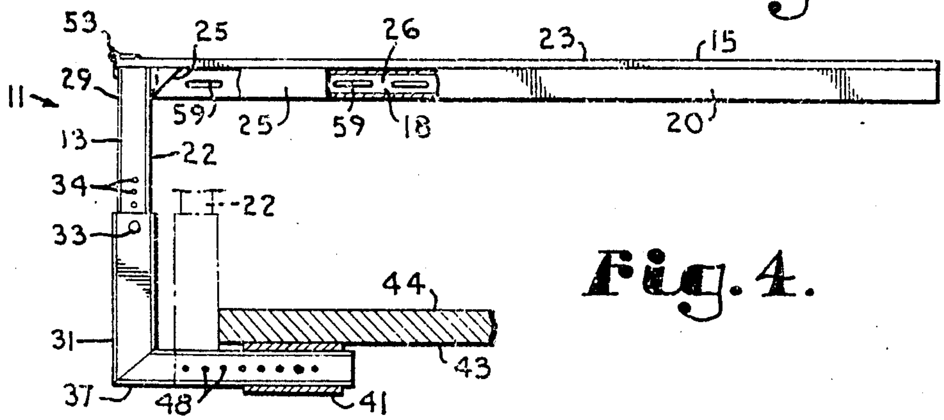
FIG. 4 is an enlarged side elevational view of the apparatus, with portions broken away to show detail thereof and with an alternative position thereof illustrated in phantom lines.

The legs 21 and 22 are joined together by an elongate cross-member 28 that is hingeably connected to the frame 20, at a front corner of the apparatus 11 and the legs 21 and 22 extend generally downwardly therefrom, see FIGS. 2 and 4. The front of the apparatus 11, in this embodiment, is designated as the side containing the rotational axis of the panel 23 containing the transparent shield 15 that extends between the tubular member section 25 (that is to the left in FIG. 4). However, the directional reference "front" and the like are for reference only and such references are not intended to limit the scope of the present invention, as any side of the device embodying the present invention could be designated as the "front" or "back".

Each of the legs 21 and 22 include upper sections 29 and 30 respectively and lower sections 31 and 32 respectively telescopically receiving respective upper sections 29 and 30. The legs 21 and 22 are contructed of rectangular cross-sectional tubing. The outside dimensions of the cross section of the legs upper sections 29 and 30 are slightly smaller than the inside dimensions of the respective lower sections 31 and 32 that are likewise constructed of rectangular cross-sectional tubing. The dimensional difference between the respective rectangular cross sections allows a closely spaced but slideable relationship between the upper sections 29 and 30 and respective lower sections 31 and 32. The telescoping relationship permits the relative adjustment of the height of the apparatus 11, see FIG. 6.

A pin 33 received through aligned apertures 34 in upper sections 29 and 30 and apertures 35 in lower sections 31 and 32 allows an adjusted height to be locked.

The apertures 34 are generally parallel and equally spaced along opposing sides of each leg upper sections 29 and 30.

The horizontal position of the apparatus 11 is likewise adjustable. The leg lower sections 31 and 32 each include respective lower support elbows 37 and 38 constructed of rigid rectangular cross-sectional tubing. The support elbows 37 and 38 are fixedly joined to the remainder of an associated leg lower section 31 and 32 at approximately a 90 degree angle. A pair of mounting brackets 41 and 42 are constructed of rigid material. The brackets 41 and 42 are secured to an underside 43 of an operating table 44 or the like. The brackets 41 and 42 form a horizontally aligned rectangular channel or receiver 45 in cooperation with the table underside 43 sized and spaced to telescopingly receive the support elbows 37 and 38 therein.

The horizontal position of the apparatus 11 with respect to the mounting environment (in this case the table 44) is adjusted by sliding the elbows 37 and 38 within the mounting brackets 41 and 42 until a selected position is found. The position is fixed using horizontal positioning pins 46. In particular, when the desired horizontal position is obtained, the horizontal positioning pins 46 are inserted through horizontally spaced adjusting apertures 48 in the elbows 37 and 38 as well as alignable apertures in the mounting brackets 41 and 42.

While the present embodiment illustrates a frame 20 having a tubular member 24 with triangular cross-section and legs 21 and 22 with rectangular cross-sections, it is foreseen that in alternative embodiment other configurations, such as circular cross-sections, could be used.

The transparent shield 15 of the present embodiment comprises the panel 23 and is preferable substantially rectangular and has a planar surface constructed of rigid, transparent plastic, see FIG. 2. The rectangular dimensions of the shield 15 generally are the same as the dimensions of the exterior of the tubular member 24 except in the front whereat the shield 15 overhangs the tubular member 24 sufficiently to align with the outer edge of the cross-member 28. The shield 15 is preferably sized to cover and contain the spread of harmful substances foreseeably emanating under pressure or propelled from a surgical incision or the like toward the upper body and face of a surgeon 50, while simultaneously allowing operating room personnel generally unobstructed working access with their hands to an incision or other working site on a patient 51, See FIG. 1. It is foreseen that the invention could be embodied in a variety of other sizes for additional applications.

The transparent shield 15 is hingedly attached to the support structure cross-member 28 by hinges 53 and 54 at the front edge of the frame 20. Rotating about the axis of the hinges 53 and 54, the transparent shield 15 may be positioned at various acute angles relative to horizontal, see phantom lines in FIG. 2. Preferably the hinges 53 and 54 are stiff and will maintain the shield 15 at a selected non-horizontal position; however, it is foreseen where the shield is too heavy for the hinges 53 and 54 that a ratchet and pawl or similar device may be used in cooperation with the hinges 53 and 54 between the frame 20 and shield 15, permitting the shield 15 to be locked in position when rotated angularly above horizontal.

The vacuum drawing system 16 includes a connector 57 extending outwardly from near one end at the front of the apparatus 11. The connector 57 is operably flow connected to the channel 26 in the tubular member 24 and through the channel 26 with a plurality of inward opening apertures 59 that open beneath but in generally surrounding relationship to the periphery or perimeter of the shield 15.

Figure 5:
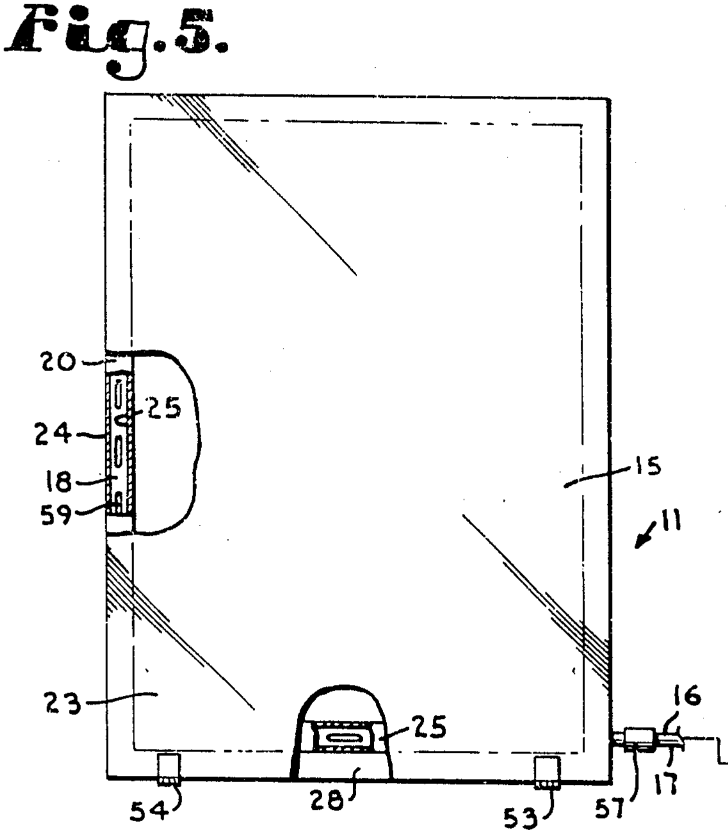
FIG. 5 is an enlarged top plan and partially schematic view of the apparatus with portions broken away to show detail thereof.

The connector 57 also operably flow connects with the vacuum conduit 17. The vacuum conduit 17 is preferably an elongate tube suitable for conveying gases drawn under a vacuum therealong without collapsing. The conduit 17 is operably connected to the vacuum generator 19 that is shown in FIG. 5 as a pump 60. Preferably, between the pump 60 and the connector 57 is a filter 61 for removing both particulate matter and liquids drawn into the vacuum conduit 17.

Figure 7:
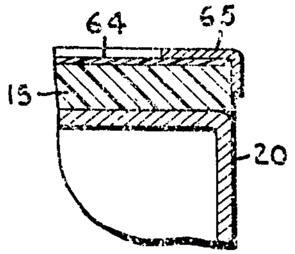
FIG. 7 is an enlarged and fragmentary cross-sectional view of the apparatus, showing a shield with a removable cover thereover.

Shown in FIG. 7 is a clear flexible cover 64 constructed of plastic or the like and extendable over the shield 15. The cover 64 can be easily removed and replaced to keep the shield 15 clean during use. A similar cover could be removeably adhered to the underside of the shield 15 that could be removed to restore visibility, if the shield is sprayed with an opaque substance.

Figure 6:
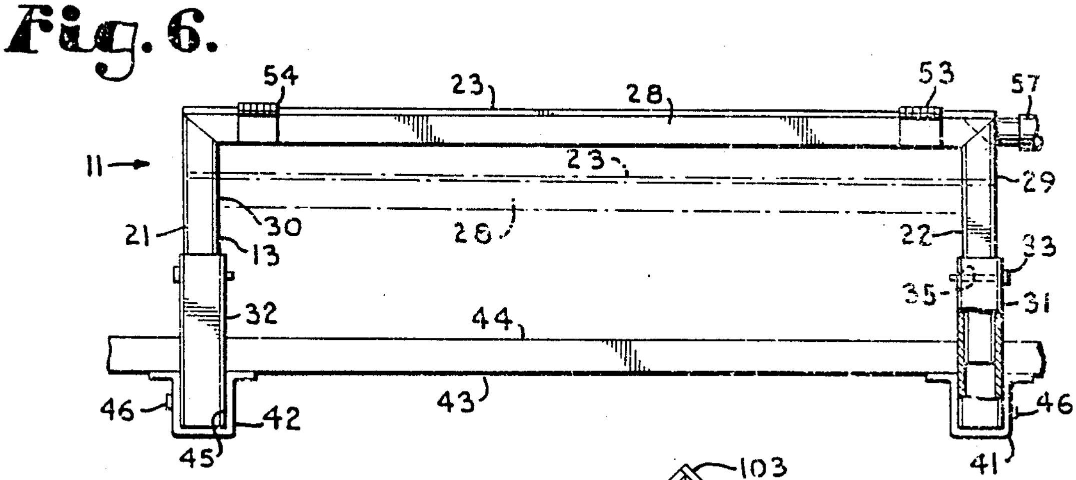
FIG. 6 is an enlarged front elevational view of the apparatus showing the shield in a first height position and showing the shield in a second height position in phantom lines with portions broken away to show detail thereof.

In use the apparatus 1 is positioned over a patient 51, having a medical procedure or the like performed thereon, as shown in FIG. 1. The angle height and horizontal position of the shield 15 may be adjusted to help protect the surgeon 50, as shown in FIGS. 2, 4 and 6. The pump 60 is started to draw substances, especially gases and aerosols containing body fluids, from under the shield 15 into the apertures 59 and subsequently through the channel 26, the connector 57, the vacuum conduit 17, the filter 61 and finally through the pump 60 with solids and liquids having been removed therefrom so as to draw such substances away from the surgeon 50, thereby substantially reducing the risk of exposure of the surgeon's mucous membranes and the like to such substances. The shield 15 also operatively prevents sprays or substances propelled with force from the site of the patient's operational procedure from striking the surgeon 50 in an unprotected area, while allowing the surgeon 50 to be able to clearly see the operational site and to work with their hands in a generally unobstructed manner at the site. In particular, the site is generally accessible from 360° surrounding same except for the relatively small field of access blocked by the legs 21 and 22.

Figure 8:
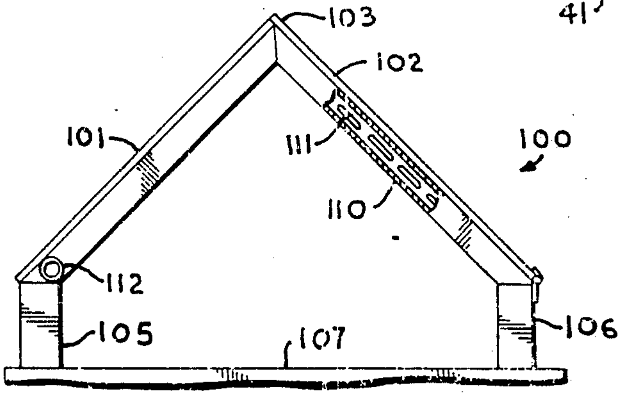
FIG. 8 is a side elevational view of a first modified protective apparatus in accordance with the present invention with portions broken away to show detail thereof.

Shown in FIG. 8 is a modified embodiment of a protective apparatus according to the present invention and generally designated by the reference numeral 100. The apparatus 100 is similar in many respects to the apparatus 1 and, therefore, only differences will be described in detail.

The apparatus 100 includes a pair of protective shields 101 and 102 joined along a common edge 103 thereof at approximately a right angle relative to each other. Support struts 105 raise the shields 101 and 102 on opposite sides thereof above a planar surface 107 to allow access beneath the edges of the shields 101 and 102. Surrounding the underside perimeter of both shields 101 and 102 is a tubular structure 110 with a plurality of apertures 111, flow connected to a vacuum system 112 similar to the vacuum system 16 of the previous embodiment. The shields 101 and 102 are sufficiently wide to cover an operational site or the like and allow a pair of medical practitioners to work with greater ease at the same site. The triangularly shaped openings beneath and to both sides of the shields 101 and 102 whereat same are joined may be covered by a clear panel to prevent escape of fluids through such openings.

It is to be understood that while certain forms of the present invention have been illustrated and described herein, it is not to be limited to the specific forms or arrangement of parts described and shown.

What is claimed and desired to be secured by Letters Patent is as follows:

1. An apparatus for reducing the potential for contamination of personnel during a procedure likely to produce both contaminated sprays and aerosols in an area of said procedure; said apparatus comprising:

(a) a transparent shield adapted to be placed in a covering relationship to the area to be isolated to form a physical barrier thereabove;

(b) a vacuum drawing conduit extending substantially around a perimeter of said shield and including a plurality of apertures spaced therealong; and (c) vacuum generating means operably connected to said vacuum drawing conduit for drawing fluids through said apertures from beneath said shield.

2. The apparatus according to claim 1 including:

(a) a support structure for supporting said shield in spaced relationship above the area.

3. The apparatus according to claim 2 wherein:

(a) said support structure includes leg means for operably connecting said structure to an operating table.

4. The apparatus according to claim 3 wherein:

(a) said leg means includes vertical position adjustment means to vertically adjust the position of said shield.

5. The apparatus according to claim 3 wherein:

(a) said leg means includes horizontal position adjustment means to horizontally position adjustment means to horizontally adjust the position of said shield.

6. The apparatus according to claim 3 wherein:

(a) said shield is hingeably connected to said support structure to allow selective positioning of said shield.

7. The apparatus according to claim 3 wherein:

(a) said support structure allows substantially unrestricted access to said area from beneath the sides of said shield.

8. The apparatus according to claim 1 wherein:

(a) said shield is substantially planar and is constructed of rigid material.

9. The apparatus according to claim 1 wherein:

(a) said vacuum generating means includes filter means to remove solids and liquids drawn with fluids through said vacuum drawing conduit.

10. The apparatus according to claim 1 wherein:

(a) said shield includes two transparent sections aligned so as to be non-planar with one another; and including;

(b) support means to support said sections above the site of a medical procedure.

11. An apparatus for preventing the exchange of harmful substances; said apparatus comprising:

(a) a transparent shield adapted to be placed in a covering relationship to an area to be isolated so as to form a physical barrier between the area and an environment thereabout;

(b) a vacuum conduit positioned substantially around and attached on an underside of the perimeter of said shield, said conduit including an internal channel;

(c) a plurality of apertures located along said vacuum conduit and communicating from beneath said shield with said internal channel in said vacuum conduit;

(d) means for generating a vacuum and communicating same with said apertures through said channel such that fluids from under said shield are urged to be drawn therethrough;

(e) means adapted to collect harmful substances after the substances are drawn into said vacuum conduit; and (f) a support structure for supporting said transparent shield.

12. The apparatus according to claim 11 wherein:

(a) said transparent shield is substantially planar and is hingedly connected to said support structure.

13. The apparatus according to claim 12 wherein:

(a) said support structure includes connection means to allow said apparatus to be removeably connected to a table; and (b) said support structure includes height adjustment means adapted to allow selective adjustment of the height of said shield above the table.

14. An apparatus for preventing the transfer of harmful substances to a practitioner during medical procedures and the like; said apparatus comprising:

(a) a substantially planar transparent shield constructed of a rigid material; said shield being adapted to be placed in a covering relationship to a source of hazardous substances;

(b) a cantilever support structure hingedly connected to one side of and supporting said shield in spaced relationship above the source; said structure having a pair of depending legs including height and horizontal adjustment means and adapted to be slideably and removeably received in mounting brackets on a table;

(c) a tubular member being positioned in generally surrounding relationship to the underside of a periphery of said shield;

(d) a plurality of spaced apertures located along said tubular member; said apertures oriented downwardly and inwardly in relation to said tubular member; said tubular member having a generally continuous internal channel flow connecting with said apertures; and (e) vacuum drawing means operably flow connected to said channel for drawing fluids from under said shield through said apertures and said channel.

15. The apparatus according to claim 14 wherein:

(a) said support structure includes means allowing same to be portable.

16. A method of preventing the exchange of harmful substances between the environment and an area to be isolated, while providing visual and hand access to the area to be isolated; said method comprising the steps (a) placing a shield in closely spaced relationship over said area; said shield having a substantially planar surface and being constructed of a generally rigid transparent material;

(b) providing a support structure for said shield to space said shield above said area;

(c) adjusting the position of said support structure to position said shield in a selected spaced relationship with respect to but generally directly above said area;

(d) providing a vacuum drawing system including a tubular member with an internal channel and apertures spaced along said member therefor flow connecting said channel with the surrounding environment;

(e) placing said tubular member in surrounding relationship to the underside of a periphery of said shield; and (f) generating a vacuum to operably draw fluids through said tubular member while said shield is in a covering relationship to said area thereby evacuating harmful substances from beneath said shield.

* * * * *